United States Patent [19]

Vora

[11] Patent Number: 4,695,662
[45] Date of Patent: Sep. 22, 1987

[54] LIGHT PARAFFIN DEHYDROGENATION PROCESS

[75] Inventor: Bipin V. Vora, Elk Grove Village, Ill.

[73] Assignee: UOP Inc., Des Plaines, Ill.

[21] Appl. No.: 848,354

[22] Filed: Apr. 4, 1986

[51] Int. Cl.$^4$ ............................ C07C 5/03; C07C 7/11
[52] U.S. Cl. ..................................... 585/324; 568/697; 585/655
[58] Field of Search .............. 585/655, 654, 324, 332, 585/331; 568/697

[56] References Cited

U.S. PATENT DOCUMENTS

| | | | |
|---|---|---|---|
| 3,527,837 | 9/1970 | Woerner et al. | 585/655 |
| 3,711,569 | 1/1973 | Tschopp et al. | 585/655 |
| 4,219,678 | 8/1980 | Oberaus et al. | 568/697 |
| 4,329,516 | 5/1982 | Al-Maddarris | 585/654 |
| 4,381,418 | 4/1983 | Gewartowski | 585/655 |
| 4,430,517 | 2/1984 | Imai et al. | 585/660 |
| 4,431,529 | 2/1984 | Carson | 208/343 |
| 4,469,811 | 9/1984 | Lucien | 502/227 |
| 4,486,547 | 12/1984 | Imai et al. | 502/223 |

OTHER PUBLICATIONS

Vora, et al., "$C_2/C_5$ Dehydrogenation Updated" *Hydrocarbon Processing*, Apr. 1982, pp. 171–174.
Sussow, S. et al., "Dehydrogenation Links LPG to More Octanes," *Oil & Gas Journal*, Dec. 8, 1980.
Muddarris, G. R., "Now, MTBE from Butane," *Hydrocarbon Processing*, Oct. 1980, p. 91.

*Primary Examiner*—Asok Pal
*Attorney, Agent, or Firm*—Thomas K. McBride; John F. Spears, Jr.

[57] ABSTRACT

A process is disclosed for the catalytic dehydrogenation of propane or butanes. The vapor phase reaction zone effluent stream is contacted with a heavy absorption liquid and then with a light absorption liquid. The light absorption liquid is composed of hydrocarbons recovered from the reaction zone effluent stream. This secondary contacting removes components of the heavy absorption liquid from the recycle gas, thus eliminating the deleterious effects of these compounds on the dehydrogenation catalyst. The heavy absorption liquid may be produced within the process by a catalytic olefin-consuming reaction zone.

9 Claims, 2 Drawing Figures

LIGHT PARAFFIN DEHYDROGENATION PROCESS

FIELD OF THE INVENTION

The invention relates to a hydrocarbon conversion process employed to convert light hydrocarbons such as butane to the corresponding olefinic hydrocarbon. More specifically, the invention relates to the recovery of a product olefinic hydrocarbon produced by the catalytic dehydrogenation of butane. The product recovery steps of the invention relate to the separation of hydrocarbons through the use of absorption and fractional distillation.

INFORMATION DISCLOSURE

Processes for the dehydrogenation of light acyclic hydrocarbons are well known to those skilled in the hydrocarbon conversion arts. For instance, the dehydrogenation of $C_2$ to $C_5$ paraffins is described in the article beginning at page 171 of the April 1982 edition of *Hydrocarbon Processing*. Because the light paraffins are relatively volatile, a more complicated separation scheme than a bulk condensation is normally required to effect the separation of the product olefins from the light by-products and hydrogen simultaneously produced in the process. It is therefore believed that U.S. Pat. No. 4,381,418 assigned to S. A. Gewartowski et al. is pertinent for its teaching of a catalytic dehydrogenation process for $C_2+$ normally gaseous paraffinic hydrocarbons and the recovery of the products of the reaction. U.S. Pat. Nos. 4,430,517 and 4,486,547 issued to T. Imai et al. and 4,469,811 issued to J. P. Lucien are believed pertinent for their teaching of catalysts and operating conditions which can be employed for the dehydrogenation of $C_2$ to $C_5$ paraffins.

A number of commercial petroleum refining processes, especially fluidized catalytic cracking or FCC units, employ a product recovery method often referred to in the art as a gas concentration unit. An example of this method of product recovery is provided in U.S. Pat. No. 4,431,529 issued to D. B. Carson. In this reference the effluent stream of the reaction zone is compressed and passed into a vapor-liquid contacting vessel. The vapor phase stream removed from this vessel is passed into an absorber used to recover the more valuable hydrocarbons such as propane, propylene, and butylene. The liquid phase material from the separation vessel is passed into a stripping column. This combination on an absorber and a stripper is widely used in the processing arts. An article appearing at page 96 of the Dec. 8, 1980 of the *Oil and Gas Journal* is pertinent for its showing of the overall flow of a light dehydrogenation process in which the numerous product recovery steps include the use of an integrated absorber and stripper. As in the previously cited reference, the vapor phase effluent of the reactor is cooled and compressed and then passed into a vapor-liquid separation vessel. The vapors emanating from this passed into the bottom of an absorber. The liquid phase material is passed directly into a deethanizer column downstream of the absorber-stripper combination. The bottoms stream of the deethanizer column is an olefin-rich product stream.

U.S. Pat. No. 4,329,516 issued to G. R. Al-Muddarris is believed pertinent for its similar teaching in regard to passage of the effluent stream of a dehydrogenation reactor into a recovery section comprising an absorption column and a desorption column. It appears from the drawing that the entire effluent of the dehydrogenation reactor is passed into the absorption column.

The above-cited U.S. patent to G. R. Al-Muddarris and the previously cited *Oil and Gas Journal* article are also believed pertinent for their teaching in regard to the usage of a paraffin dehydrogenation reactor in preparing olefinic feedstocks for passage into an etherification zone. Specifically, they teach the production of isobutylene which may be passed into a zone for reaction with methanol and the production of methyl tertiary butyl ether (MTBE).

An article appearing at page 91 of the October 1980 edition of *Hydrocarbon Processing* is believed pertinent for its teaching of the overall flow involved in an integrated process for the production of MTBE from normal butanes. This overall flow includes the recycling of unconsumed isobutane from the etherification zone to the dehydrogenation zone. U.S. Pat. No. 4,219,678 issued to F. Obenaus et al. is believed pertinent for its teaching of the operation of an etherification zone specific to the production of MTBE by the reaction of isobutene with methanol.

BRIEF SUMMARY OF THE INVENTION

The invention provides a process for the production of acyclic olefinic hydrocarbon which in certain instances will be highly advantageous in that it will have a lower capital cost than the processes heretofore presented. The invention also provides an improved process in relation to other processes which employ absorption for the recovery of the desired products. This improved result is obtained through the use of a heavier absorption liquid to achieve a greater degree of recovery coupled with the use of a light absorbent liquid which is generated in the product recovery section of the process. The light absorption liquid removes residual components of the heavy absorption liquid from the vapor stream emanating from the overall absorption step of the process, thereby minimizing or eliminating adverse effects such as the deactivation which may occur when these heavier compounds of the heavy absorption liquid enter the dehydrogenation zone as by being present in the recycle gas stream.

One broad embodiment of the invention may be characterized as a process for the dehydrogenation of paraffinic hydrocarbons which comprises the steps of: passing a feed stream comprising a butane into a catalytic dehydrogenation zone maintained at dehydrogenation conditions and producing a dehydrogenation reaction zone effluent stream comprising $C_3$ and $C_4$ paraffins and $C_3$ and $C_4$ olefins; contacting the dehydrogenation reaction zone effluent stream in sequence with a first process stream comprising a $C_5$-plus compound in a first absorption zone and with a second process stream comprising propane in a second absorption zone and producing a hydrogen-rich gas stream, which comprises hydrogen and propane, and at least one rich liquid stream comprising the $C_5$-plus compound, $C_3$ and $C_4$ paraffins and $C_3$ and $C_4$ olefins; passing a portion of the hydrogen-rich gas stream into the dehydrogenation zone as a recycle gas stream; passing the rich liquid stream into a fractionation zone comprising a depropanizer column and a debutanizer column, and separating the compounds entering the fractionation zone into at least a depropanizer column net overhead stream comprising propane, a debutanizer column net overhead stream comprising $C_4$ olefins and paraffins and a debutanizer column net bottoms stream comprising the $C_5$-plus compound; passing at least a portion of the debutanizer column net bottoms stream into the first absorption zone as said first process stream; passing at least a portion of the depropanizer column net overhead stream into the second absorption zone as said second process stream; and removing the debutanizer column overhead from the process as a product stream.

DETAILED DESCRIPTION

Figure 1:
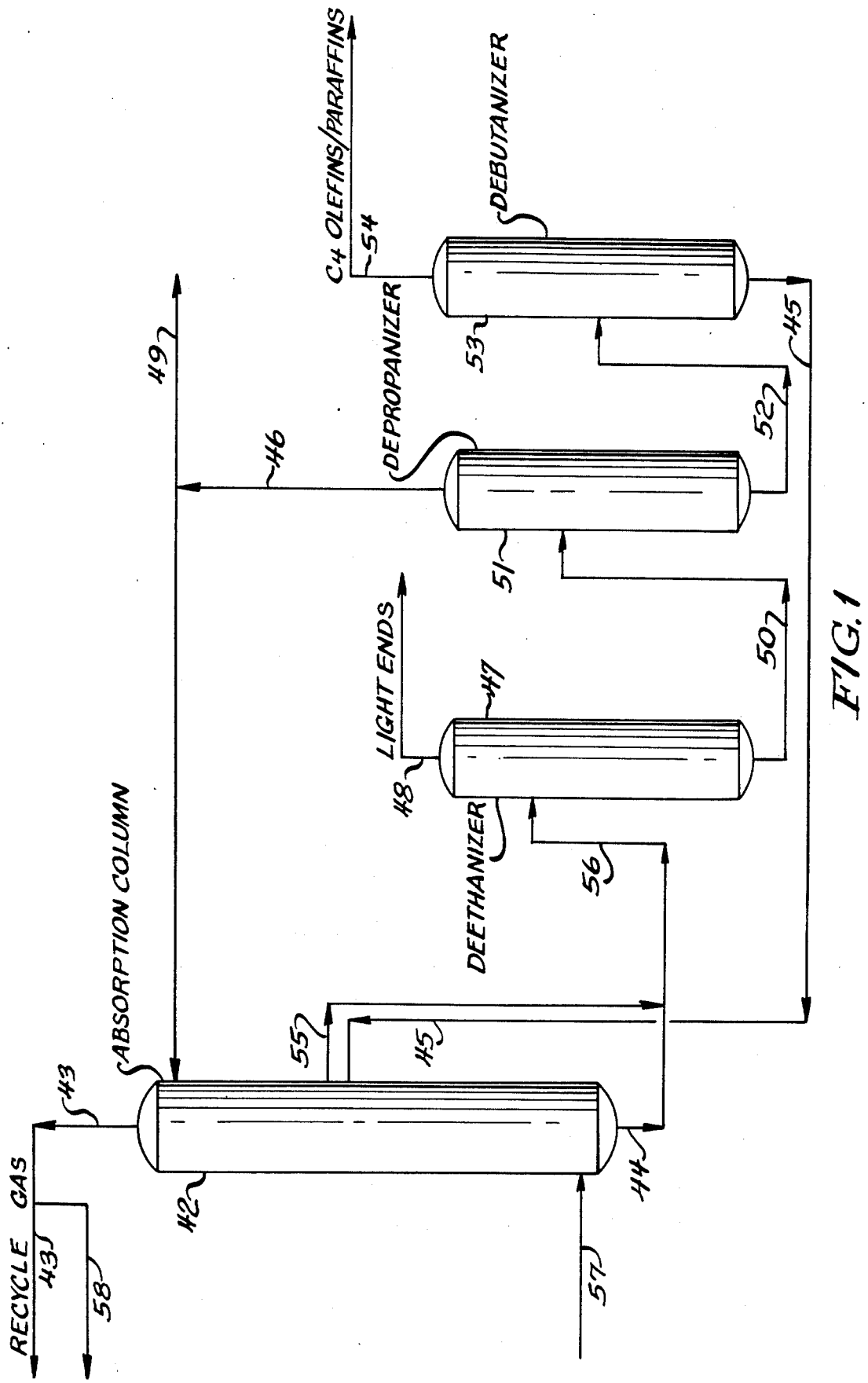
FIG. 1 is a simplified process flow diagram illustrating the recovery of a hydrogen-rich gas and a product stream comprising $C_4$ olefins from a dehydrogenation reaction zone effluent stream fed to absorption column 42 through line 57.

Olefinic hydrocarbons are one of the major building blocks of a large number of petrochemical products. Olefinic hydrocarbons are also used in petroleum refineries for the production of motor fuel blending components. The subject process finds utility in providing a process for the production of these light olefinic hydrocarbons. The subject invention also finds utility as a process for the production of various ethers formed by the reaction of a light olefin with an alcohol, such as the formation of methyl tertiary butyl ether (MTBE) by the reaction of isobutylene with methanol.

It is an objective of the subject invention to provide a process for the production of light olefins having three or four carbon atoms per molecule. It is a further objective of the subject invention to provide a process which employs absorption to recover the product $C_3+$ hydrocarbons from the effluent stream of a catalytic dehydrogenation zone. It is a specific objective of the subject invention to provide a method of employing a complex of equipment referred to as a gas concentration plant, which complex was employed to recover and separate the effluent stream of a fluidized catalytic cracking process, as the product recovery facilities of a paraffin dehydrogenation zone.

The feed streams to the subject process will comprise one or more light paraffins having three or four carbon atoms per molecule. The feed stream will therefore preferably comprise propane or butane or a mixture of propane and butane. The feed stream may also contain limited amounts of ethane and pentanes. It is preferred that the concentration of ethane in the feedstream is less than 10 mole percent. It is also preferred that the concentration of pentane is less than 20 mole percent. The feedstream may comprise an admixture of several different hydrocarbons such as a mixture of propane, normal butane and isobutane or the feedstream may be comprised of a single hydrocarbon species such as a high-purity stream of propane or isobutane.

In the subject process the entire effluent stream of the dehydrogenation reactor is passed into an absorption zone wherein it is contacted with an absorption liquid comprising $C_5+$ compounds such as $C_5+$ hydrocarbons or ethers. A typical heavier absorption liquid would be a naphtha boiling range mixture of hydrocarbons derived from crude oil. This heavier absorption liquid is internally recycled within the process in a loop comprising the absorption zone and a fractionation column or columns employed as a stripping zone, although in one embodiment of the subject invention the lean absorption liquid may also circulate through a reaction zone wherein at least one component of the absorption liquid is produced.

This preliminary absorption step also produces a vapor phase stream which is removed from the absorption zone. An essential step in the subject process is the contacting of this vapor phase stream with a second absorption liquid. The second absorption liquid is a lighter liquid which is internally produced within the process. The function of the second absorption step is the removal of the minor but significant amount of the heavier absorption compounds from the vapor phase stream. The reason for this removal step is that the vapor phase stream is the precursor for the hydrogen recycle stream employed in the process, and the heavier compounds may in some instances have deleterious effects upon the dehydrogenation catalyst such as the promotion of the formation of carbonaceous deposits on the catalyst often referred to as coking or other causes of catalyst deactivation.

Referring now to the drawings, FIG. 1 illustrates one particular embodiment of the invention. This embodiment will be described first since FIG. 1 is simpler than FIG. 2 which illustrates several embodiments and the entire flow of the overall process. The Figures have been simplified by the deletion of such well known equipment as control systems, reboilers, overhead condensers, vessel internals, pumps, etc. which are within the capabilities of those skilled in the art to provide. These presentations of some embodiments of the invention are not intended to exclude from the scope of the invention other embodiments set out herein or which are obvious variations of those embodiments.

In FIG. 1, the compressed and cooled entire effluent of the dehydrogenation reaction zone is passed through line 57 into the bottom of an absorption column 42. When processing a $C_4$ feedstream, the stream of line 57 will comprise $C_4$ olefins and paraffins, which may be iso- or normal hydrocarbons depending upon the charge stock to the dehydrogenation zone, and will also comprise propane, propylene, a small amount of light ends such as methane and ethane produced as by-products of the dehydrogenation reaction and hydrogen which is also produced in a dehydrogenation reaction. Hydrogen is often considered a valuable by-product of the reaction. The gaseous effluent stream is passed upward within the absorption column countercurrent to a descending liquid phase stream. The absorption column will contain vessel internals such as trays or packing material or a combination of both trays and packing material designed to promote the intimate admixing and contacting of the descending liquid phase and the ascending vapor phase. This contacting step is performed at absorption promoting conditions of temperature and pressure which result in a transfer of a very great majority of the $C_4$ and $C_3$ hydrocarbons originally present in the reaction zone effluent stream into the descending liquid phase stream. Preferably at least 90 mole percent of the $C_3$ and $C_4$ hydrocarbons are in this manner picked up by the descending liquid.

The liquid flowing downward through the lower contacting zone of the absorption column is collected at the bottom of a column and removed through line 44. This stream of the heavy absorption liquid is admixed with a stream of a lighter absorption liquid from line 55 and passed through line 56 into a light ends stripping column or deethanizer 47. The light ends such as methane and ethane are separated from the entering hydrocarbon mixture by fractional distillation within the deethanizer and are discharged from the process as a light ends stream carried by line 48. The remaining hydrocarbons, basically $C_3$ and $C_4$ hydrocarbons plus the heavy absorption liquid are discharged from the deethanizer in line 50 and passed into a depropanizer column 51. The depropanizer column is operated at conditions which effect the separation of the entering compounds into a net overhead stream discharged through line 46 and a net bottoms stream removed through line 52. The net overhead stream of line 46 is preferably a highly concentrated stream of $C_3$ hydrocarbons. The stream will therefore comprise propane and propylene. A portion of the net overhead stream is withdrawn from the process through line 49 as a net propylene-containing product stream. The remaining portion continues through line 46 and is passed into an upper point of the upper contacting zone of the overall absorption column 42. This portion of the depropanizer net overhead stream functions as the light absorption liquid employed within the absorption column.

The net bottoms stream of the depropanizer column is passed through line 52 into a debutanizer column, which is operated at conditions effective to separate the entering compounds into a net overhead stream comprising $C_4$ hydrocarbons and a net bottoms stream comprising heavier boiling hydrocarbons and essentially free of $C_4$ olefins or paraffins. The net overhead stream of the debutanizer column 53 is withdrawn through line 54 as the primary product stream of the process and passed into the appropriate recovery facilities or downstream process unit which consumes the $C_4$ olefins. The net bottoms stream of the debutanizer is passed through line 45 into an intermediate point of the stacked absorption column 42 to serve as the heavy absorption liquid used in the lower first contacting zone for the removal of $C_3$ and $C_4$ hydrocarbons from the reaction zone effluent stream.

The contacting of the heavier absorption liquid passed into column 42 via line 45 with the ascending vapor stream will result in an equilibrium concentration of the component of the heavier absorption liquid entering and becoming a part of the rising vapor stream. The contacting of the vapor stream with the light absorbent liquid formed within the process, in this case the liquid phase stream of propane and propylene removed from the top of the depropanizer column, is intended to remove these heavier hydrocarbons from the vapor phase stream. This removal function is performed in the upper second absorption zone located in the upper portion of the unitary absorption column 42. These heavier hydrocarbons are thereby removed from the light preferably hydrogen-rich gas discharged form the absorption column through line 43. The recycled gas is preferably split into two portions with a first portion being recycled to the reaction zone and the second portion being withdrawn from the process through line 58.

Those skilled in the art will recognize that the operating conditions maintained within the absorption zones must be chosen based on the composition of the vapors entering the zones and the composition of the absorption liquid streams. It is self-evident that the use of a propane-containing liquid phase absorption liquid will necessitate the use of elevated pressures and/or reduced temperatures. The two absorption zones are preferably operated at approximately the same pressures, differing of course due to inherent pressure drops through vessels and process lines, but at different temperatures. A general range of operating pressures is from about 1.7 to about 35 atm. gauge (25 to 500 psig) with a preferred pressure range being from 3.5 to 17 atm. gauge (50 to 250 psig). A preferred range of operating temperatures for the first absorption zone is from about 15 to 50 degrees Celsius. A preferred range of operating temperatures for the second absorption zone is from about $-18$ to about 27 degrees Celsius. It is preferred that the rich liquid emanating from the second absorption zone is not commingled with liquid present within the first absorption zone but is instead withdrawn from any unitary column as a separate sidecut or trapped out stream. Intercoolers may be located within the absorption zone and especially between the absorption zones.

Figure 2:
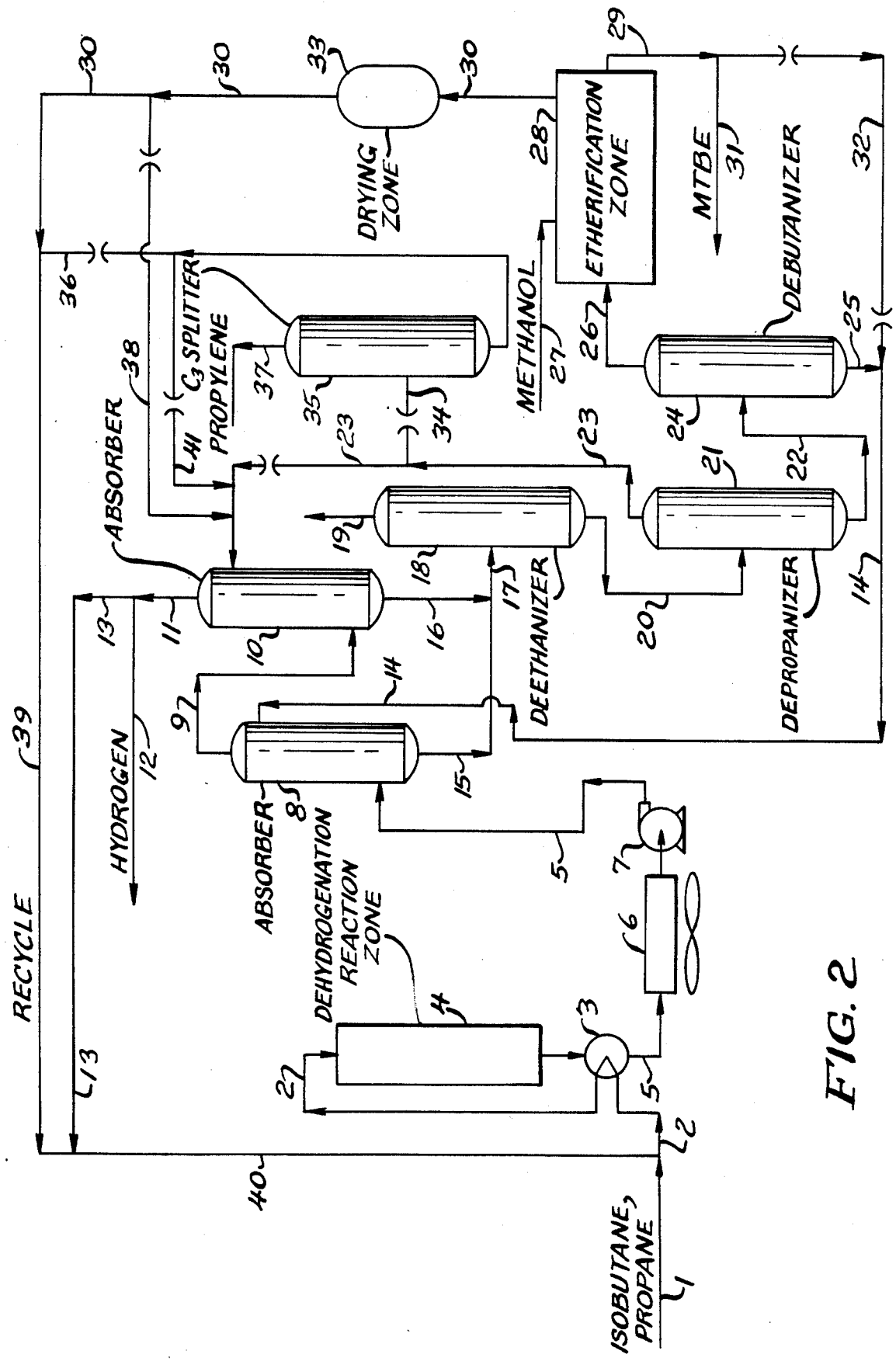
FIG. 2 is a simplified process flow diagram illustrating several embodiments of the invention including the use of an etherification zone 28 and a propylene-propane splitter column 35.

FIG. 2 illustrates various embodiments of the subject invention. In the Drawing those lines which are broken, with the breaks being set off by two opposing curved lines, are optional lines which may not be employed in some embodiments described herein. It is pertinent to note that some of the fractionation columns illustrated on the Drawing such as the $C_3$ splitter column 35 and the debutanizer column 24 may also be dispensed with in some embodiments of the invention as set out below.

Referring now to FIG. 2, a feedstream comprising isobutane and propane enters the process through line 1. The feedstream is admixed with a recycle stream of $C_4$ hydrocarbons from line 39 and recycle hydrogen-rich gas from line 13, with these two recycle streams being delivered to the feedstream via line 40. The combined reaction zone charge admixture flows into line 2 and is passed through an indirect heat exchange means 3 wherein it is heated with heat recovered from the reaction zone effluent stream. The charge admixture is then preferably further heated through means of a direct fired heater not shown which may be within the overall dehydrogenation reaction zone 4. The charge admixture is then contacted with a suitable dehydrogenation catalyst at dehydrogenation-promoting conditions, preferably in the manner set out below. Contact with the catalyst at these conditions is effective to result in the dehydrogenation of a significant portion of the entering paraffinic hydrocarbons and the production of a dehydrogenation reaction zone effluent stream carried by line 5 which comprises an admixture of hydrogen, each of the entering feed hydrocarbons, and olefinic hydrocarbons and olefinic hydrocarbons corresponding to each of the feed paraffins. The effluent stream will therefore comprise in this embodiment hydrogen, propane, isobutane, propylene and isobutylenes. The reaction zone effluent stream is first cooled for heat recovery in the feed-effluent heat exchange means 3 and then continues through line 5 to an air cooled heat exchanger 6. Significant cooling is desired to allow the downstream absorption to be performed at a reasonable pressure. The effluent of the heat exchanger is then compressed in the compressing means 7 and passed through line 5 into a first absorber 8. In some instances it may be desired to further cool the effluent of the compressor to remove the heat of compression. However, it is specifically preferred that the dehydrogenation reaction zone effluent stream is not cooled to the extent that will result in any significant condensation. In this manner the entire dehydrogenation reaction zone is passed into the first absorption zone 8 as a vapor phase stream.

Within the absorption zone 8, the entire reaction zone effluent stream is contacted with a descending stream of a heavy absorption liquid entering through line 14. Substantial quantities, preferably over 90 mole percent of the $C_3$ and $C_4$ hydrocarbons, present in the reaction zone effluent stream of line 5 become absorbed into the descending liquid and are removed from the absorber through line 15. The remaining gaseous portions of the reaction zone effluent stream together with an equilibrium concentration of the heavy absorption liquid stream of line 14 leaves the absorber 8 through line 9 and is passed into a second absorber 10. In the second absorber the entering vapors are contacted with a descending liquid in a manner similar to the procedure performed in the first absorber. However, in the second absorber a lighter, that is, lower molecular weight, absorption liquid is employed. This absorption liquid enters the second absorber through line 23. The second absorption liquid will remove from the rising vapors essentially all of the heavy compounds present in this gas stream due to the contacting between the vapor and the heavy absorption liquid in the first absorber. The absorption stream of line 23 plus absorbed compounds such as propane, isobutane and the heavier compounds of the heavy absorption stream are removed from the bottom of the second absorber through line 16. There is thereby formed a hydrogen-rich process stream removed through line 11. This vapor phase stream is preferably divided into a hydrogen-rich off-gas stream discharged from the process through line 12 and a hydrogen-containing recycle stream recirculated through line 13.

Those skilled in the art will recognize that the streams carried by lines 15 and 16 may be passed into the deethanizer column 18 at separate points to optimize the fractionation performed within the deethanizer. These two rich absorber liquid streams may also be combined with the resultant admixture being passed through line 17 into the deethanizer 18. The deethanizer column is designed and operated to separate the entering materials into a net bottomsstream removed through line 20 which is substantially free of $C_2$- compounds and a net overhead stream withdrawn from the process through line 19. The net overhead stream of line 19 should contain essentially all of the $C_2$ and more volatile compounds entering the deethanizer. The stream of line 19 should therefore comprise essentially all of the ethane, ethylene and methane entering the deethanizer.

The net bottoms stream of the deethanizer column 18 is passed into a depropanizer column 21. The depropanizer column 21 is designed and operated to separate the entering materials by boiling point into a net bottoms stream withdrawn through line 22, and comprising the $C_4+$ boiling point materials entering the column, and a net overhead stream withdrawn through line 23. The net overhead stream of line 23 will comprise essentially all of the propane and propylene entering the depropanizer column.

The treatment of the net overhead stream of the depropanizer column is subject to variation. For instance, the entire net overhead stream may be passed through line 34 into a $C_3$ splitter column 35. The material flowing through line 34 is therein separated into a net overhead stream comprising propylene withdrawn through line 37 and a net bottom stream comprising propane withdrawn through line 36. The exact amount or concentration of propylene in the net overhead stream is determined by an economic consideration of the cost of extensive fractional distillation facilities versus the desire for high-purity propylene streams. Preferably the net overhead stream of line 37 will contain at least 90 mole percent propylene. It is also preferred that the net bottomsstream of line 36 will contain less than 20 mole percent propylene. The propylene of the net overhead stream is a highly valuable product of the process. The amount of propylene produced will be dependent basically upon the concentration of propane in the feedstream of line 1, although a small but significant amount of propylene is produced during the dehydrogenation of $C_4$ hydrocarbons. It is therefore foreseeable that the propylene splitter would be employed in a process charging solely $C_4$ hydrocarbons. The bottomsstream of the $C_3$ splitter column may be also handled in different ways. It is therefore contemplated to pass the entire net bottoms stream carried by line 36 through lines 41 and 23 into the second absorber 10 as the light absorption liquid. Alternatively all or a part of the depropanizer bottoms stream may be recycled to the dehydrogenation reactor through lines 36 and 39.

The net bottoms liquid stream of the depropanizer 21 is passed into the optional debutanizer column 24 through line 22. As described herein the debutanizer is optional since the entire bottoms stream of the depropanizer may be passed directly into the etherification zone 28. The compounds charged to the debutanizer are separated therein into a net bottoms stream removed through line 25 comprising the higher boiling hydrocarbons and a net overhead stream removed through line 26 which comprises all of the entering compounds which have boiling points equivalent to or less than the $C_4$ hydrocarbons fed to the debutanizer 24. The bottomsstream of the debutanizer column will, in the preferred embodiments of the invention, contain the heavy absorption liquid such as the naphtha boiling range components which are used as the heavy absorption stream charged to the first absorber 8 through line 14.

The overhead stream of line 26 will contain unconverted isobutane and other $C_4$ paraffins present in the feedstream of line 1 and the resultant products of the dehydrogenation of the $C_4$ hydrocarbons. This net overhead stream is passed into the etherification zone and admixed with methanol from line 27 prior to being contacted with a suitable catalyst. The details of the etherification procedure are described below. The result of this contacting step is the selective reaction of methanol with isobutylene to produce methyl tertiary butyl ether (MTBE). Various fractionation columns are preferably located within the etherification zone 28. These fractionation columns are used to separate the effluent of the reactor into at least two streams. The unreacted $C_4$ hydrocarbons entering the etherification zone are concentrated into a stream discharged through line 30, normally referred to as the etherification zone raffinate stream, and an etherification zone product or effluent stream carried by line 29.

It is preferred that the total content of line 29 is withdrawn from the process through line 31 as an MTBE product stream. Alternatively, in those embodiments of the invention wherein the heavy absorption liquid comprises MTBE, a portion of the MTBE may be passed through line 32 to the junction with line 14 for the purpose of providing makeup MTBE to the absorber 8. This makeup stream would be utilized when the debutanizer column 24 is employed within the process. It is also contemplated that the debutanizer column 24 could be deleted and a portion of the liquid flowing through line 29 could be passed into line 32 and eventually to the first absorber 8 as the heavy absorption liquid. In this instance, the material flowing through line 29 is divided between the product stream of line 31 and the lean heavy absorption liquid of line 32.

The $C_4$ raffinate stream discharged from the etherification zone 28 through line 30 is preferably first passed through a drying zone 33. The drying zone may also effect the removal of oxygenates from the raffinate stream. These oxygenates are such compounds as methanol, by-product ethers and MTBE. Information on the operation of the drying zone is provided in the references cited herein and to some extent below. After passing through the drying zone, the $C_4$ raffinate stream may be passed entirely into line 39. In this instance, the entire raffinate stream is recycled to the dehydrogenation reaction zone 4. All or a portion of the net bottoms stream of the $C_3$ splitter column flowing through line 36 may be admixed with the $C_4$ raffinate stream of line 30. Alternatively, a portion of the $C_4$ raffinate stream may be passed through optional line 38 into line 23 to form the light absorption liquid employed in the second absorber 10. In this instance, it would be preferred that none of the overhead of the depropanizer column 21 is employed as the light absorption liquid. In this instance, the entire overhead stream of the depropanizer 23 would be passed into the $C_3$ splitter column 35, with the propylene being withdrawn from the process and the propane being recycled for conversion.

It is therefore evident that the light absorption liquid is generated at some point within the product recovery facilities of the dehydrogenation reaction zone. It is also evident that there are many variations possible in the arrangement of the fractionation columns employed in the product recovery section and in the various process flows and compositions of the material employed as the light and the heavy absorption liquids. The preferred fractionation columns and the arrangement of the columns will be to some extent dictated by the composition of the feedstream and the conversion achieved in the dehydrogenation reactor. However, it is contemplated that the overall process flow will normally utilize a depropanizer column since during the dehydrogenation of butane a small but significant amount of $C_3$ hydrocarbons is formed.

The dehydrogenation zone employed in the process will contain a reaction zone and associated auxiliary process equipment such as fired heaters, control systems, catalyst regeneration facilities, etc. The reaction zone preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction zone. A detailed description of moving bed reactors of this type may be obtained by reference to U.S. Pat. Nos. 3,647,680; 3,706,536; 3,825,116; 3,839,196; 3,839,197; 3,854,887; 3,856,662; and 3,978,150.

The particular dehydrogenation conditions employed within the reaction zone may vary depending on such factors as the catalyst activity, feed carbon number, and the desired conversion. The reaction zone conditions normally employed for propane and butane dehydrogenation include a temperature of from about 500 to 700 degrees Celsius, a pressure of from 0.5 to about 10 atmospheres and a liquid hourly space velocity of about 1 to 20. The preferred operating temperature will be within the range of from about 550 to 660 degrees Celsius, and the preferred operating pressure is about 0.5 to 2 atmospheres. The preferred dehydrogenation catalyst is comprised of a platinum group component, preferably platinum, a tin component and an alkali metal component with a porous inorganic carrier material. Other catalytic compositions may be used within this zone if desired. The preferred catalyst contains an alkali metal component chosen from cesium, rubidium, potassium, sodium and lithium. The preferred alkali metal is normally chosen from lithium and potassium, with potassium being preferred for isobutane. Preferred dehydrogenation catalysts comprise an alkali metal and a halogen such as potassium and chlorine in addition to the tin and platinum group components. The preparation and use of dehydrogenation catalysts is well known to those skilled in the art and further details as to suitable catalyst compositions are available in patents, such as those cited above, and other standard references (U.S. Pat. Nos. 4,486,547; 4,438,288).

In order to increase the supply of isobutane available to certain embodiments of the process and also to convert the nonreactive normal paraffins of the recycle stream the normal butanes of the $C_4$ raffinate stream may be passed into a butane isomerization unit. The normal butanes are preferably first concentrated into an isomerization zone feed stream in a deisobutanizer column.

In one form of the overall integrated process, the olefins recovered from the effluent stream of the dehydrogenation reaction zone are fed to an etherification zone together with a feed alcohol. Alcohols other than methanol such as ethanol, propanol, ethylene, glycol or propylene glycol can be charged to the process. Ethers such as methyl tertiary amyl ether or ethyl tertiary amyl ether can be produced. The etherification zone may take many different forms but is preferably similar to that described in U.S. Pat. No. 4,219,678 and shown in the previously cited paper. In this instance the isobutane or other isoolefin, methanol or other feed alcohol, and a recycle stream containing the product ether, and methanol are passed into the reaction zone in which they are contacted with an acidic catalyst while maintained at etherification conditions. A wide range of materials is known to be effective as etherification catalysts for the preferred reactants including mineral acids such as sulfuric acid, boron trifluoride, phosphoric acid on kieselguhr, phosphorus-modified zeolites and various sulfonated resins. The use of a sulfonated solid resin catalyst is preferred. These resin-type catalysts include the reaction products of phenol-formaldehyde resins and sulfuric acid and sulfonated polystyrene resins including those cross-linked with divinylbenzene. Further information on suitable etherification catalysts may be obtained by reference to U.S. Pat. Nos. 2,480,940; 2,922,822; and 4,270,929 and the previously cited etherification references.

A broad range of etherification conditions includes a superatmospheric pressure sufficient to maintain the reactants as a liquid phase, generally below about 200 psig, and a temperature between about 30 degrees and about 100 degrees Celsius. A preferred temperature range is from 50 to 100 degrees Celsius. The reaction rate is normally faster at higher temperatures but conversion is more complete at lower temperatures. High conversion in a moderate volume reaction zone can therefore be obtained if the initial section of the reaction zone, e.g. the first two-thirds, is maintained above 70 degrees Celsius and the remainder of the reaction zone is maintained below 50 degrees Celsius. This may be accomplished most easily with two reactors. The ratio of feed alcohol to isoolefin should normally be maintained in the broad range of from 1:1 to 2:1. With the preferred reactants good results are achieved if the ratio of methanol to isobutene is between 1.1:1 and 1.5:1. An excess of methanol above that required to achieve satisfactory conversion at good selectivity should be avoided.

In the subject process oxygen-containing hydrocarbonaceous compounds, and possibly other compounds as described below, are preferably removed from the raffinate stream when the raffinate stream is recycled to the dehydrogenation reaction zone by contacting the effluent stream with a sorbent solid. The sorbent, which may function as a physical or as a chemical adsorbent, is preferably disposed as a fixed bed in two or more cylindrical contacting chambers. The flow of the recycle stream is preferably switched between different chambers to allow continuous processing of the recycle stream while the sorbent in the chambers which are not being used is either regenerated or replaced depending on the regenerability and remaining capacity of the sorbent. The sorbent may also be contained in a different chamber configuration such as a moving bed or a fluidized bed.

The required sorption-promoting conditions will depend on such factors as the specific sorbent used in the process and the chemical compounds to be removed from the recycle stream. A general range of suitable sorption-promoting conditions includes a superatmospheric pressure less than about 500 psig, although higher pressures may be employed, and a temperature less than about 160 degrees Fahrenheit (71 degrees Celsius). A liquid hourly space velocity of less than 10 hr.$^{-1}$ should be employed. A preferred range of sorption-promoting conditions includes a pressure between 10 and about 200 psig, a temperature between 10 and 150 degrees Fahrenheit (10 and 65 degrees Celsius) and a liquid hourly space velocity between 0.3 and 3.0 hr$^{-1}$.

The sorbent is preferably in the form of solid spherical particles on the order of about 1/16 to ¼ of an inch in diameter. The preferred sorbents are the zeolitic materials known as molecular sieves and ion exchange resins. It is contemplated that the solid sorbent may also be chosen from the group consisting of natural and synthetic aluminas, clays and charcoals and other known sorbents. The preferred sorbents are type 5A and type 13X molecular sieves which should remove both the oxygen-containing impurities and any sulfur compounds such as dimethylsulfoxide which may be present due to the admixture of a feed stream with the hydrocarbonaceous effluent stream. A type 3A molecular sieve may be employed to remove water from the recycle hydrocarbon stream. Further description of dehydrogenation, etherification and adsorptive treating of $C_4$ raffinate streams may be obtained by reference to U.S. Pat. Nos. 4,575,567 and 4,465,870 which are incorporated herein by reference.

One embodiment of the invention may accordingly be characterized as a hydrocarbon conversion process, which process comprises the steps of passing a feed stream comprising a $C_4$ paraffin into a catalytic dehydrogenation reaction zone maintained at dehydrogenation conditions and producing a dehydrogenation reaction zone effluent stream comprising hydrogen, a $C_3$ and the $C_4$ paraffin and a $C_3$ and a $C_4$ olefin; passing the dehydrogenation reaction zone effluent stream upward through a first absorption zone countercurrent to a first process stream comprising a $C_5$-plus compound, and producing a lean vapor stream, which stream comprises hydrogen, the $C_5$-plus compound and the $C_3$ olefin, and a first rich liquid stream comprising the $C_5$-plus compound, $C_3$ and $C_4$ paraffins and $C_3$ and $C_4$ olefins; passing the lean vapor stream upward through a second absorption zone countercurrent to a second process stream which comprises a $C_3$–$C_4$ paraffin, and producing a hydrogen-rich gas stream, which stream comprises hydrogen and a $C_3$–$C_4$ paraffin, and a second rich liquid stream which comprises the $C_5$-plus compound and the $C_3$ olefins; passing the first and the second rich liquid streams into a fractionation zone and separating the first and the second rich liquid streams into at least a first net overhead stream comprising propane, and a third process stream comprising a $C_4$ olefin and a $C_4$ paraffin; and, passing at least a portion of the third process stream into a catalytic reaction zone wherein at least a portion of the $C_4$ olefin is consumed in the creation of a product compound, and producing an effluent stream comprising the $C_4$ paraffin and a product stream comprising the product compound.

What is claimed:

1. A hydrocarbon conversion process, which process comprises the steps of:
  (a) passing a feed stream comprising a $C_4$ paraffin into a catalytic dehydrogenation reaction zone maintained at dehydrogenation conditions and producing a dehydrogenation reaction zone effluent stream comprising hydrogen, a $C_3$ and a $C_4$ paraffin and a $C_3$ and a $C_4$ olefin;
  (b) passing the dehydrogenation reaction zone effluent stram upward through a first absorption zone countercurrent to a first process stream comprising a $C_5$-plus compound, and producing a lean vapor stream, which stream comprises hydrogen, the $C_5$-plus compound and the $C_3$ olefin, and a first rich liquid stream comprising the $C_5$-plus compound, $C_3$ and $C_4$ paraffins and $C_3$ and $C_4$ olefins;
  (c) passing the lean vapor stream upward through a second absorption zone countercurrent to a second process stream which comprises a $C_3$–$C_4$ paraffin, and producing a hydrogen-rich gas stream, which stream comprises hydrogen and a $C_3$–$C_4$ paraffin, and a second rich liquid stream which comprises the $C_5$-plus compound and the $C_3$ olefins;
  (d) recycling at least a portion of the hydrogen-rich gas stream to the catalytic dehydrogenation reaction zone;
  (e) passing the first and the second rich liquid streams into a fractionation zone and separating the first and the second rich liquid streams into at least a first net overhead stream comprising propane, and a third process stream comprising a $C_4$ olefin and a $C_4$ paraffin; and,
  (f) passing at least a portion of the third process stream into a catalytic etherification zone wherein at least a portion of the $C_4$ olefin is consumed by reaction with methanol in the creation of a $C_5$-plus ether, and producing an effluent stream comprising the $C_4$ paraffin and a product stream comprising the $C_5$-plus ether.

2. The process of claim 1 further characterized in that the fractionation zone comprises a depropanizer column which produces said first net overhead stream, and in that at least a portion of the first net overhead stream is passed into the second absorption zone as the second process stream.

3. The process of claim 1 further characterized in that the $C_5$-plus compound present in the first process stream is the $C_5$-plus ether produced in the etherification zone.

4. The process of claim 1 further characterized in that the fractionation zone also comprises a deethanizer column and in that a stream comprising ethane is removed from the deethanizer column and withdrawn from the process.

5. The process of claim 1 wherein the fractionation zone comprises a depropanizer column, which produces said first net overhead stream, and a propanepropylene splitter column which receives said first net overhead stream, with a second net overhead stream comprising propane being withdrawn from the splitter column and passed into the second absorption zone as said second process stream.

6. The process of claim 5 further characterized in that the fractionation zone comprises a depropanizer column, which produces said first net overhead stream, and a debutanizer column which produces said third process stream as a net overhead stream.

7. The process of claim 6 further characterized in that at least a portion of a net bottoms stream produced by the debutanizer column is passed into the first absorption zone as said first process stream.

8. The process of claim 1 further characterized in that a portion of the effluent stream is passed into the second absorption zone as said second process stream.

9. A hydrogen conversion process, which process comprises the steps of:
(a) passing a feed stream comprising a $C_4$ paraffin into a catalytic dehydrogenation reaction zone maintained at dehydrogenation conditions and producing a dehydrogenation reaction zone effluent stream comprising hydrogen, a $C_3$ and the $C_4$ paraffin and a $C_3$ and a $C_4$ olefin;
(b) passing the dehydrogenation reaction zone effluent stream upward through a first absorption zone countercurrent to a first process stream comprising a $C_5$-plus plus ether, and producing a lean vapor stream, which stream comprises hydrogen, the $C_3$ olefin and the $C_5$-plus ether, and a first rich liquid stream comprising the $C_5$-plus ether, $C_3$ and $C_4$ paraffins and $C_3$ and $C_4$ olefins;
(c) passing the lean vapor stream upward through a second absorption zone countercurrent to a hereinafter characterized second process stream, and producing a hydrogen-rich gas stream and a second rich liquid stream, which second rich stream comprises the $C_5$-plus ether and a $C_3$–$C_4$ olefins;
(d) recycling at least a portion of the hydrogen-rich gas stream to the dehydrogenation reaction zone;
(e) passing the first and the second rich liquid atreams into a fractionation zone comprising a depropanizer column and separating the first and the second rich liquid streams into at least a first net overhead stream comprising propane and a first net bottoms stream comprising the $C_4$ olefin and the $C_5$-plus compound;
(f) passing at least a portion of the first net overhead stream into the second absorption zone as said second process stream;
(g) passing the first net bottoms stream into a catalytic etherification zone wherein at least a portion of the $C_4$ olefin is consumed in a reaction with monohydric $C_1$–$C_3$ alcohol which produces the $C_5$-plus ether and producing an etherification zone effluent stream comprising the $C_5$-plus ether; and,
(h) passing a first portion of the etherification zone effluent stream into the first absorption zone as said first process stream, and removing a second portion of the etherification zone effluent stream from the process as a product stream.

* * * * *